United States Patent
Son et al.

(10) Patent No.: US 7,619,246 B2
(45) Date of Patent: Nov. 17, 2009

(54) ORGANIC LIGHT EMITTING COMPOUND AND ORGANIC LIGHT EMITTING DEVICE COMPRISING THE SAME

(75) Inventors: Jhun-Mo Son, Yongin-si (KR); Eun-Sun Yu, Anyang-si (KR); O-Hyun Kwon, Seoul (KR); Young-Mok Son, Hwaseong-si (KR); Yu-Jin Kim, Suwon-si (KR)

(73) Assignee: Samsung Mobile Display Co., Ltd., Giheung-Gu, Yongin-City, Gyunggi-Do (KR)

(*) Notice: Subject to any disclaimer, the term of this patent is extended or adjusted under 35 U.S.C. 154(b) by 84 days.

(21) Appl. No.: 11/635,024

(22) Filed: Dec. 7, 2006

(65) Prior Publication Data

US 2007/0176541 A1 Aug. 2, 2007

(30) Foreign Application Priority Data

Jan. 27, 2006 (KR) .................. 10-2006-0009031

(51) Int. Cl.
```
H01L 35/24    (2006.01)
H01L 51/00    (2006.01)
C07D 279/10   (2006.01)
C07D 279/12   (2006.01)
C07D 295/00   (2006.01)
C07D 498/02   (2006.01)
C07D 498/12   (2006.01)
```

(52) U.S. Cl. ..................... 257/40; 544/56; 544/101
(58) Field of Classification Search .............. None
See application file for complete search history.

(56) References Cited

U.S. PATENT DOCUMENTS 4,356,429 A 10/1982 Tang

FOREIGN PATENT DOCUMENTS

JP 11-003782 1/1999

OTHER PUBLICATIONS

Kuwabara et al., "Thermally Stable Multilayered Organic Electroluminescent Devices Using Novel Starburst Molecules, 4,4',4''-Tri(N-carbazolyl)triphenylamine (TCTA) and 4,4',4''-Tri(3-methylphenylphenyl-amino)triphenylamine (m-MTDATA), as Hole-Transport Materials", Adv. Mater. 1994, 6, No. 9, pp. 677-679.

*Primary Examiner*—James O Wilson
*Assistant Examiner*—Noble Jarrell
(74) *Attorney, Agent, or Firm*—Robert E. Bushnell, Esq.

(57) ABSTRACT

A compound represented by Formula 1 and an organic light emitting device including the same:

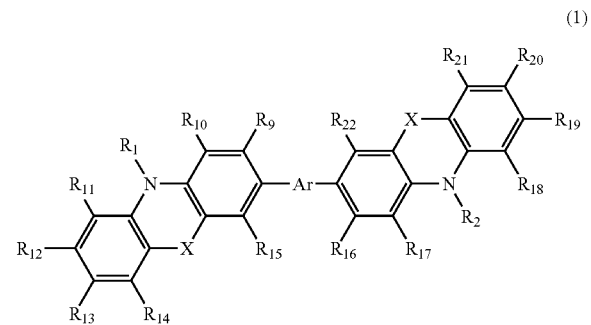

(1)

where Ar is a substituted or unsubstituted $C_6$-$C_{26}$ aryl group; X is O, S,

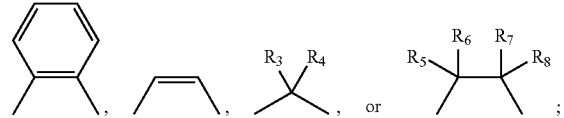

$R_1$ and $R_2$ are hydrogen, a halogen, a $C_1$-$C_{12}$ alkyl group, a $C_6$-$C_{26}$ aryl group, or a substituted group thereof; $R_3$, $R_4$, $R_5$, $R_6$, $R_7$ and $R_8$ are each independently hydrogen or a substituted or unsubstituted $C_1$-$C_{12}$ alkyl group; $R_9$ through $R_{22}$ are each independently hydrogen, a $C_1$-$C_{30}$ alkyl group, a $C_1$-$C_{30}$ alkoxy group, a $C_6$-$C_{30}$ aryl group, a $C_6$-$C_{30}$ arylalkyl group, a $C_6$-$C_{30}$ aryloxy group, a $C_5$-$C_{30}$ heteroaryl group, a $C_5$-$C_{30}$ heteroarylalkyl group, a $C_5$-$C_{30}$ heteroaryloxy group, a $C_5$-$C_{20}$ cycloalkyl group, a $C_5$-$C_{30}$ heterocycloalkyl group, or a substituted group thereof. An organic light emitting device using the compound has low operating voltage, high color purity, and high efficiency.

17 Claims, 3 Drawing Sheets

ORGANIC LIGHT EMITTING COMPOUND AND ORGANIC LIGHT EMITTING DEVICE COMPRISING THE SAME

CROSS-REFERENCE TO RELATED PATENT APPLICATION AND CLAIM OF PRIORITY

This application claims the benefit of Korean Patent Application No. 10-2006-0009031, filed on Jan. 27, 2006, in the Korean Intellectual Property Office, the disclosure of which is incorporated herein in its entirety by reference.

BACKGROUND OF THE INVENTION

1. Field of the Invention

The present invention relates to an organic light emitting compound and an organic light emitting device including the same, and more particularly, to an organic light emitting compound having excellent electric properties, thermal stability, and photochemical stability such that an organic light emitting device using the organic light emitting compound has low operating voltage and color purity and an organic light emitting device including an organic layer formed of the organic light emitting compound.

2. Description of the Related Art

Light-emitting devices are devices that generate and emit light and have wide angles of light emission, excellent contrast, and short response times. Light emitting devices can be categorized into inorganic light emitting devices having light emitting layers formed of inorganic compounds and organic light emitting devices (OLEDs) having light emitting layers formed of organic compounds. OLEDs have high brightness, low operating voltages, and short response times, and can realize emission of a large range of colors of light, when compared to inorganic light emitting devices. As a result, a lot of research into OLEDs has been conducted.

In general, an OLED has a layered structure of anode/organic light emitting layer/cathode. In addition, an OLED can have various layered structures such as a structure of anode/hole injection layer/hole transport layer/light emitting layer/electron transport layer/electron injection layer/cathode or a structure of anode/hole injection layer/hole transport layer/light emitting layer/hole blocking layer/electron transport layer/electron injection layer/cathode.

Materials used to manufacture OLEDs can be categorized into vacuum deposition materials and solution coating materials according to a method of preparing a corresponding organic layer. A vacuum deposition material should have a vapor pressure of $10^{-6}$ torr or higher at 500° C. or less and may be a small molecular material having a molecular weight of 1200 or less. A solution coating material should have high solubility with respect to a solvent such that it can be prepared in a liquid state and should include an aromatic family or heterocyclic materials.

When an OLED is manufactured using a vacuum deposition method, a vacuum system is required and thus manufacturing costs are increased, and when a shadow mask is used to define a pixel used for displaying natural color, it is difficult to obtain a pixel having high resolution. On the other hand, a solution coating method, such as an inkjet printing method, a screen printing method, or a spin coating method, can be easily used, is inexpensive, and can be used to obtain a relatively higher pixel resolution than when a shadow mask is used.

However, among materials that can be used in a solution coating method, blue light emitting molecules exhibit inferior thermal stability and color purity compared to materials that can be used in a vacuum deposition method. In addition, even when blue light emitting molecules have high thermal stability and high color purity, an organic layer formed of the blue light-emitting molecules is gradually crystallized such that the size of the formed crystals corresponds to a wavelength of visible light. As a result, visible rays are dispersed, a whitening effect takes place, and pinholes may be formed. Thus the corresponding device may easily deteriorate.

In Japanese Patent Laid-open Publication No. 1999-003782, anthracene substituted for 2 Naphthyl groups is disclosed as a compound which can be used in an light emitting layer or a hole injection layer. However, a solvent solubility of anthracene is insufficient and an organic light emitting device including such compound exhibits inferior performance.

Accordingly, improvements are required to develop an organic light emitting device having low operating voltage, high brightness, high efficiency, and high color purity using a blue light emitting compound which has good thermal stability and can be used to form an organic layer with good quality.

SUMMARY OF THE INVENTION

The present invention provides an organic light emitting compound having excellent solubility and thermal stability and an organic light emitting device having improved operating voltage, high efficiency, and color purity.

According to an aspect of the present invention, there is provided an organic light emitting compound represented by Formula 1:

[Formula 1]

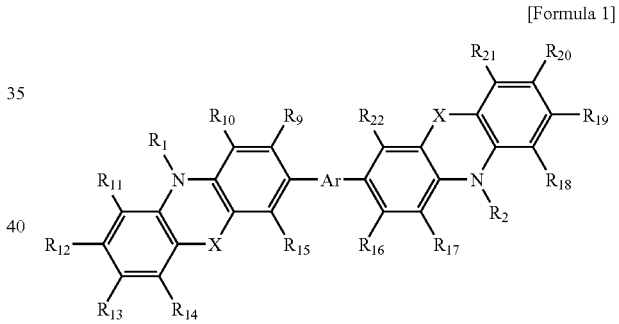

where Ar is a substituted or unsubstituted $C_6$-$C_{26}$ aryl group;

X is O, S,

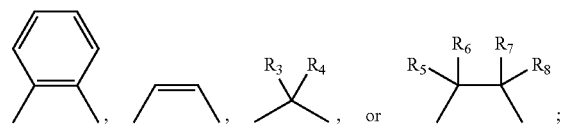

$R_1$ and $R_2$ are hydrogen, halogen, a substituted or unsubstituted $C_1$-$C_{12}$ alkyl group, or a substituted or unsubstituted $C_6$-$C_{26}$ aryl group;

$R_3$, $R_4$, $R_5$, $R_6$, $R_7$ and $R_8$ are each independently hydrogen or a substituted or unsubstituted $C_1$-$C_{12}$ alkyl group; and $R_9$ through $R_{22}$ each independently selected from the group consisting of hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ arylalkyl group, a substituted or unsubstituted $C_6$-$C_{30}$ aryloxy group, a substituted or unsubstituted $C_5$-$C_{30}$ heteroaryl group, a substituted or unsubstituted $C_5$-$C_{30}$ heteroarylalkyl group, a substituted or unsubstituted $C_5$-$C_{30}$ heteroaryloxy group, a substituted or unsubstituted $C_5$-$C_{20}$ cycloalkyl group, and a substituted or unsubstituted $C_5$-$C_{30}$ heterocycloalkyl group.

The organic light emitting compound may have the structure represented by Formula 2.

[Formula 2]

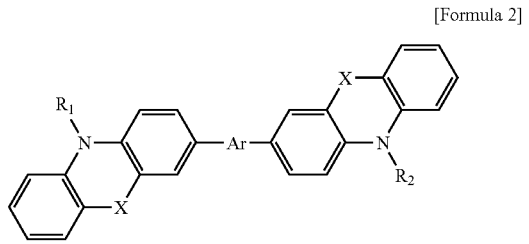

where Ar is a substituted or unsubstituted $C_6$-$C_{26}$ aryl group;
X is O, S,

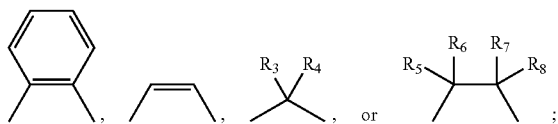

$R_1$ and $R_2$ are hydrogen, halogen, a substituted or unsubstituted $C_1$-$C_{12}$ alkyl group, or a substituted or unsubstituted $C_6$-$C_{26}$ aryl group; and $R_3$, $R_4$, $R_5$, $R_6$, $R_7$ and $R_8$ are each independently hydrogen or a substituted or unsubstituted $C_6$-$C_{12}$ alkyl group.

According to another aspect of the present invention, there is provided an organic light emitting device including: a first electrode; a second electrode; and at least one organic layer including the compound described above interposed between the first electrode and the second electrode.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
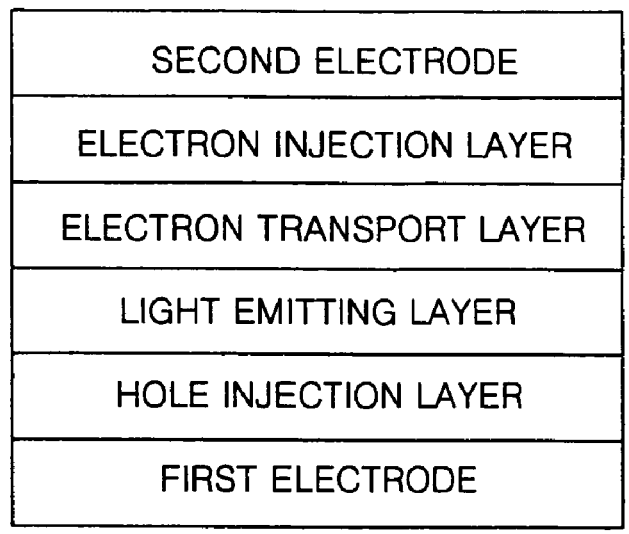
FIGS. 1A through 1C are schematic sectional views of organic light emitting devices according to embodiments of the present invention.

Hereinafter, embodiments of the present invention will be described more fully.

An organic light emitting compound according to an embodiment of the present invention is represented by formula 1:

<Formula 1>

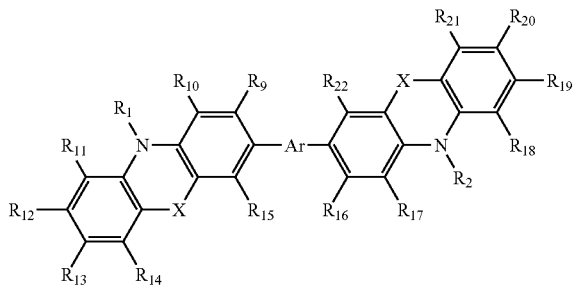

where Ar is a substituted or unsubstituted $C_6$-$C_{26}$ aryl group; X is O, S,

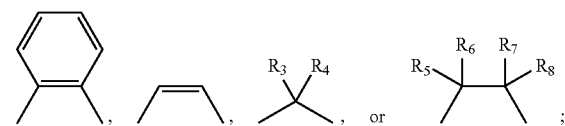

$R_1$ and $R_2$ are hydrogen, a halogen, a substituted or unsubstituted $C_1$-$C_{12}$ alkyl group, or a substituted or unsubstituted $C_6$-$C_{26}$ aryl group; $R_3$, $R_4$, $R_5$, $R_6$, $R_7$, and $R_8$ are each independently hydrogen or a substituted or unsubstituted $C_1$-$C_{12}$ alkyl group; and $R_9$ through $R_{22}$ are each independently selected from the group consisting of hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ arylalkyl group, a substituted or unsubstituted $C_6$-$C_{30}$ aryloxy group, a substituted or unsubstituted $C_5$-$C_{30}$ heteroaryl group, a substituted or unsubstituted $C_5$-$C_{30}$ heteroarylalkyl group, a substituted or unsubstituted $C_5$-$C_{30}$ heteroaryloxy group, a substituted or unsubstituted $C_5$-$C_{20}$ cycloalkyl group, and a substituted or unsubstituted $C_5$-$C_{30}$ heterocycloalkyl group.

The organic light emitting compound may have the structure represented by Formula 2 below.

<Formula 2>

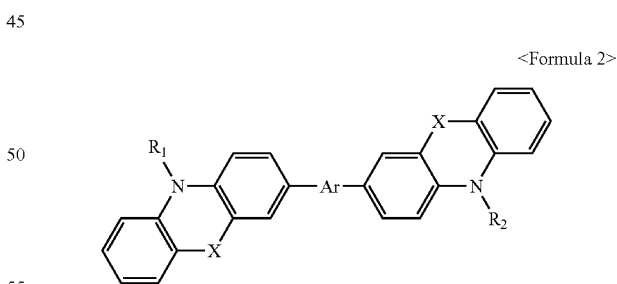

where Ar is a substituted or unsubstituted $C_6$-$C_{26}$ aryl group;
X is O, S,

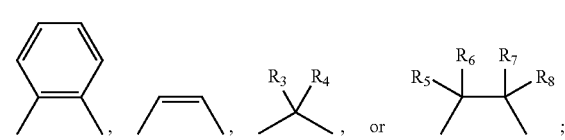

$R_1$ and $R_2$ are hydrogen, a halogen, a substituted or unsubstituted $C_1$-$C_{12}$ alkyl group, or a substituted or unsubstituted $C_6$-$C_{26}$ aryl group; and $R_3$, $R_4$, $R_5$, $R_6$, $R_7$, and $R_8$ are each independently hydrogen or a substituted or unsubstituted $C_6$-$C_{12}$ alkyl group.

The organic light emitting compound may have the structure represented by Formula 3 or Formula 4.

[Formula 3]

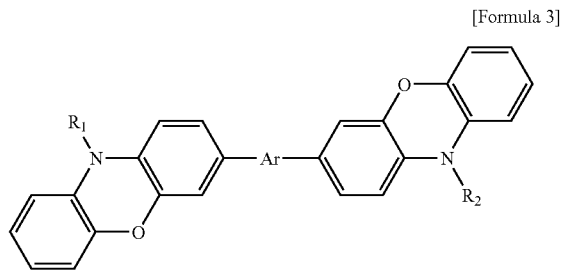

[Formula 4]

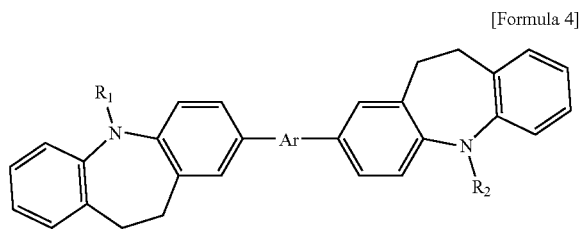

where in Formulas 3 and 4, Ar is a substituted or unsubstituted $C_6$-$C_{26}$ aryl group; and $R_1$ and $R_2$ are hydrogen, a halogen, a substituted or unsubstituted $C_1$-$C_{12}$ alkyl group, or a substituted or unsubstituted $C_6$-$C_{26}$ aryl group.

Ar may be 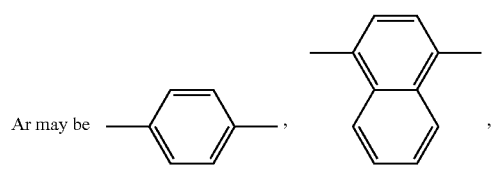,

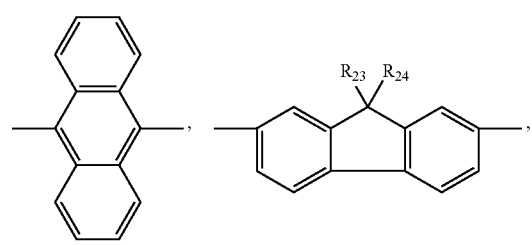

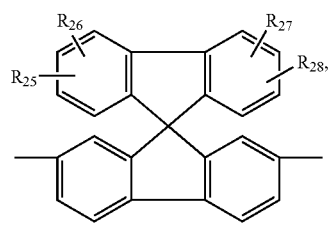

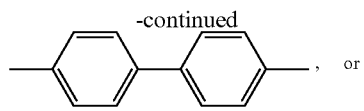, or

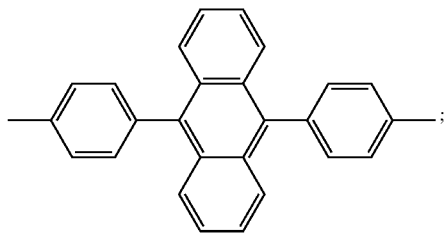;

where $R_{23}$, $R_{24}$, $R_{25}$, $R_{26}$, $R_{27}$, and $R_{28}$ are each independently hydrogen, a substituted or unsubstituted $C_1$-$C_{12}$ alkyl group, or a substituted or unsubstituted $C_1$-$C_{12}$ alkoxy group.

Examples of an unsubstituted alkyl group which is a substituent used in the embodiments of the present invention are methyl, ethyl, propyl, isobutyl, sec-butyl, tert-butyl, pentyl, iso-amyl and hexyl wherein at least one hydrogen atom of the alkyl group can be substituted for a hydroxy group, a nitro group, a cyano group, a substituted or unsubstituted amino group (—$NH_2$, —NH(R), —N(R')(R''), where R' and R'' are each independently a $C_1$-$C_{10}$ alkyl group), an amidino group, hydrazine, hydrazone, a carboxyl group, a sulfonic acid group, a phosphate group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The aryl group which is one of the substituents used in a compound of the embodiments of the present invention refers to a carbocyclic aromatic system including at least one aromatic ring where the ring may be attached or fused using a pendent method. Examples of the aryl group are an aromatic group such as phenyl, naphthyl, and tetrahydronaphthyl and at least one hydrogen atom of the aryl group can be substituted for a substituent in the same manner as described above for the alkyl group.

The term 'substituted', used when defining a substituent in a Formula representing the embodiments of the present invention refers to "substituted" with any substituent, and examples of the substituent are a $C_1$-$C_{12}$ alkyl group, a $C_1$-$C_{12}$ alkoxy group, halogen atom such as fluorine and chlorine, a $C_1$-$C_{30}$ lower alkylamino group, a hydroxy group, a nitro group, a cyano group, a substituted or unsubstituted amino group (—$NH_2$, —NH(R), —N(R')(R''), wherein R' and R'' are each independently a $C_1$-$C_{12}$ alkyl group), a carboxyl group, a sulfonic acid group, a phosphate group, a $C_1$-$C_{20}$ halogenated alkyl group, an alkenyl group, an alkynyl group, a heteroalkyl group, a $C_6$-$C_{30}$ aryl group, an arylalkyl group, a heteroaryl group, or a $C_2$-$C_{30}$ heteroarylalkyl group.

According to an embodiment of the present invention, the organic light emitting compound may have the structure represented by Formulas 5 through 21 below, but is not limited thereto:

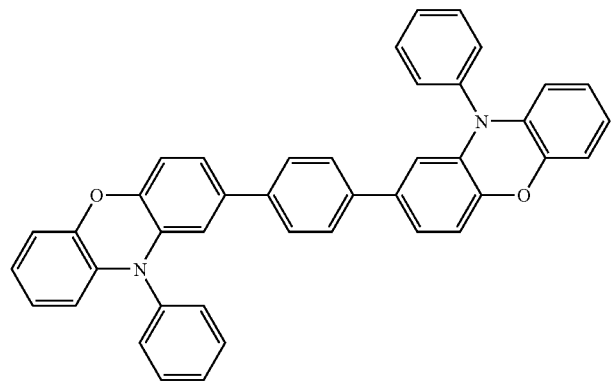
[Formula 5]
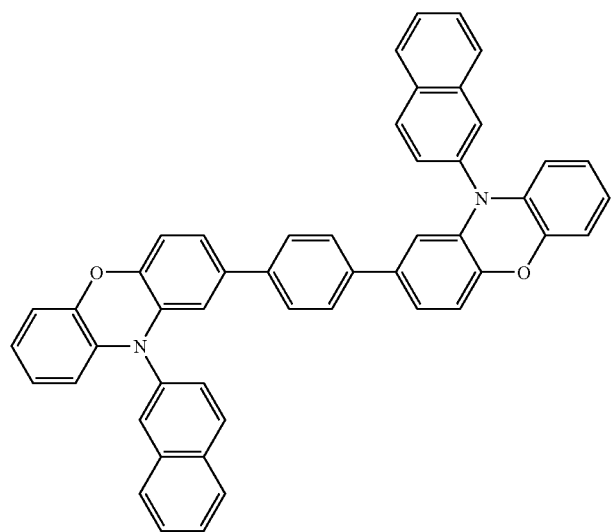
[Formula 6]
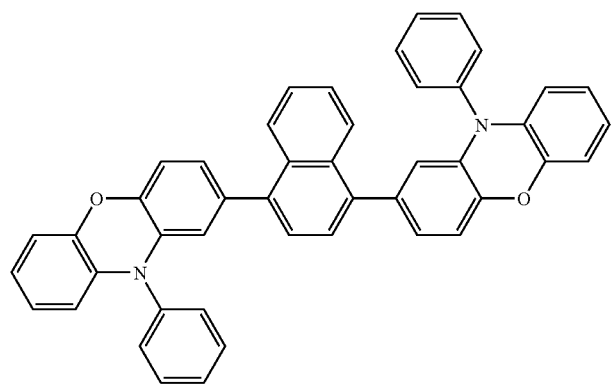
[Formula 7]

-continued
[Formula 8]
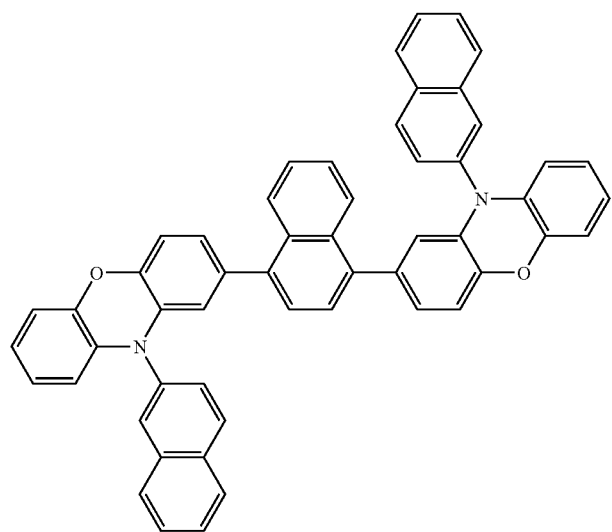
[Formula 9]
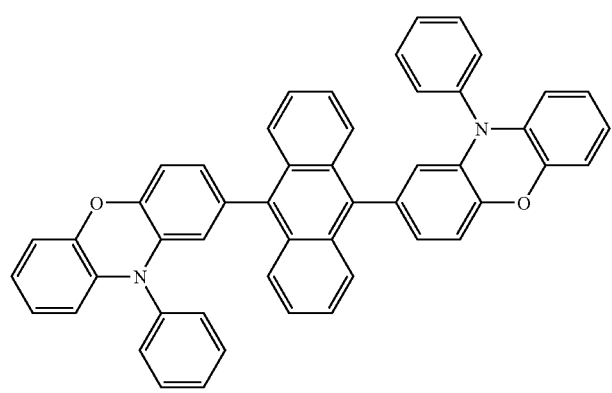
[Formula 10]
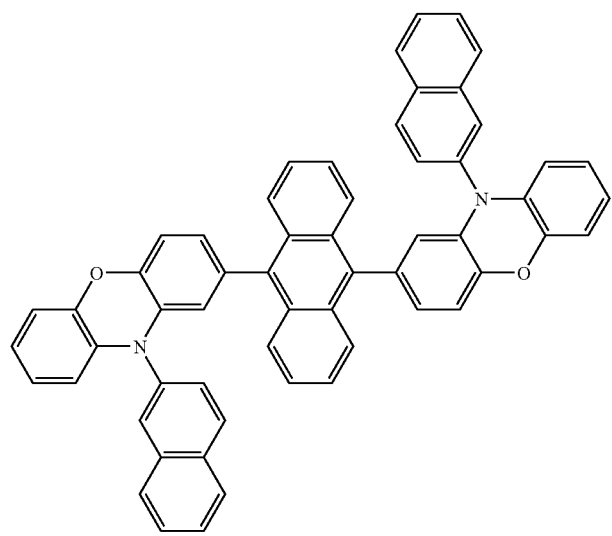

-continued
[Formula 11]
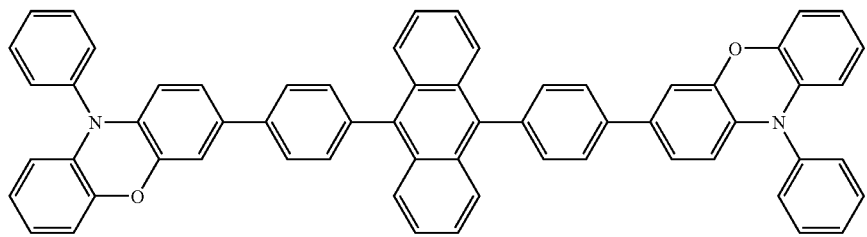
[Formula 12]
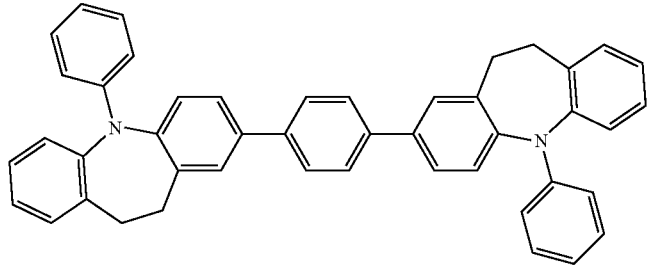
[Formula 13]
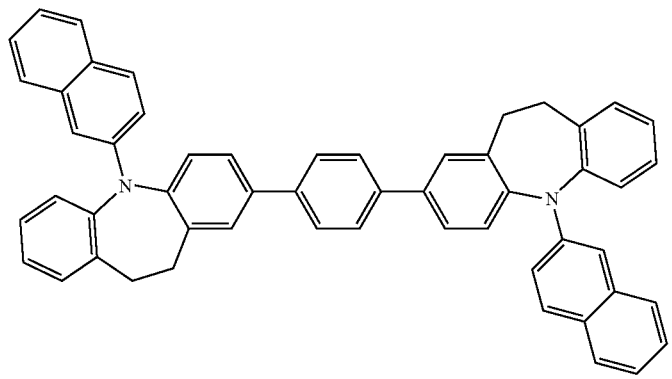
[Formula 14]
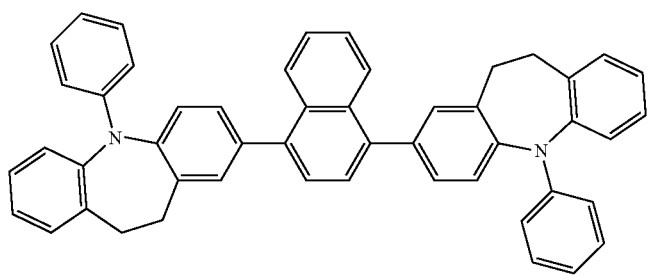
[Formula 15]
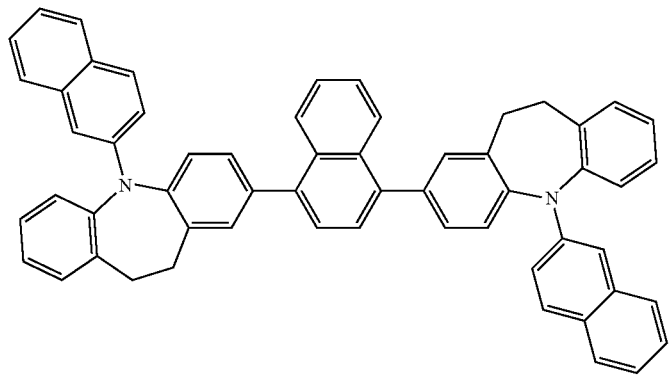

[Formula 16]
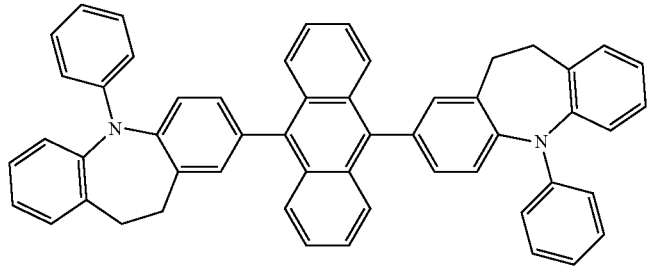
[Formula 17]
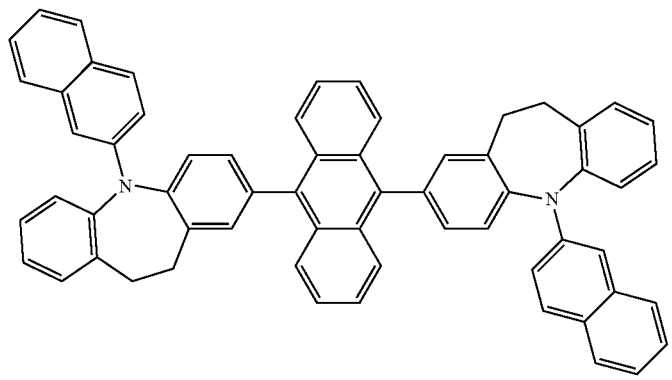
[Formula 18]
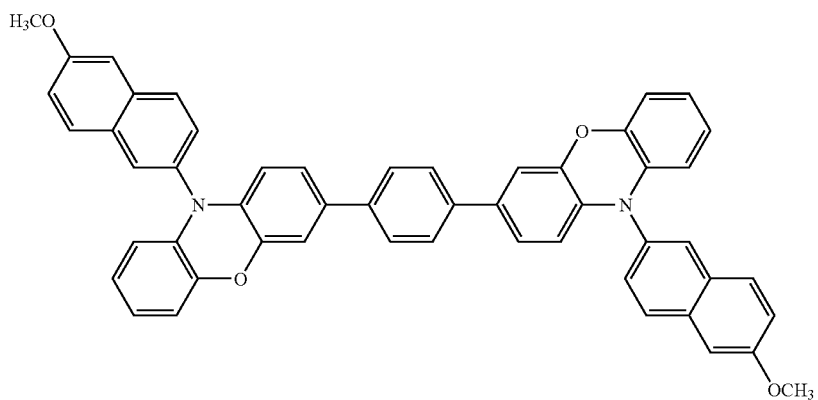
[Formula 19]
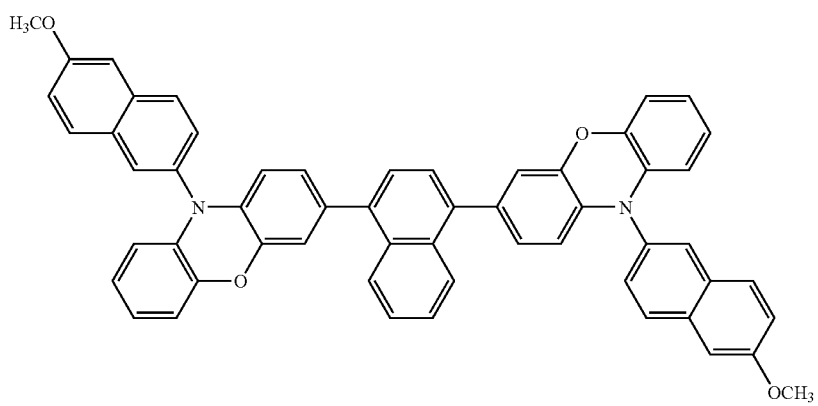

[Formula 20]

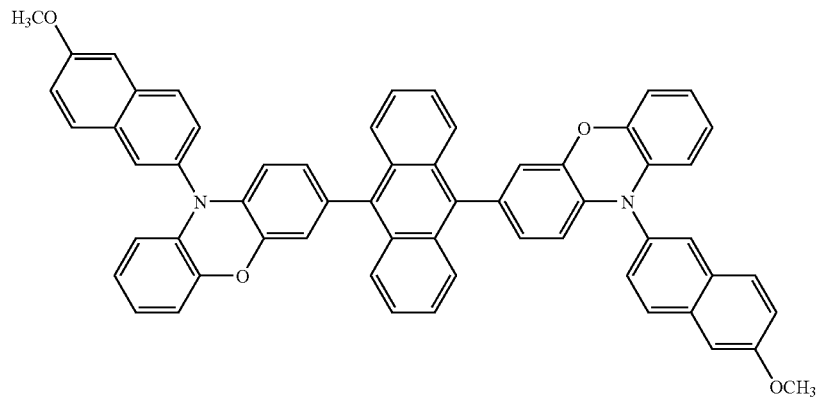

[Formula 21]

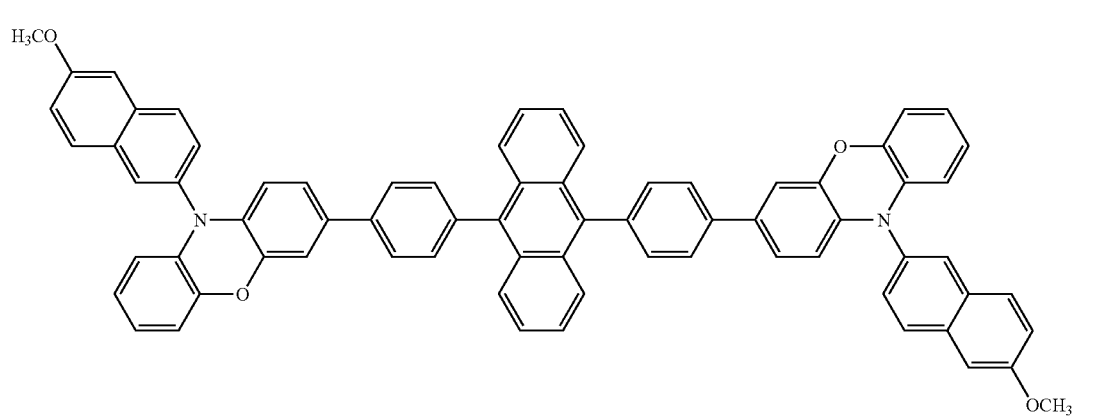

The compound represented by Formula 1 may be synthesized using a conventional synthesizing method and in particular, a method with reference to Reaction Scheme 1 in Synthesis Example 1 below.

An organic light emitting device according to an embodiment of the present invention includes a first electrode, a second electrode, and an organic layer interposed between the first electrode and the second electrode. The organic layer may include a compound represented by Formula 1.

<Formula 1>

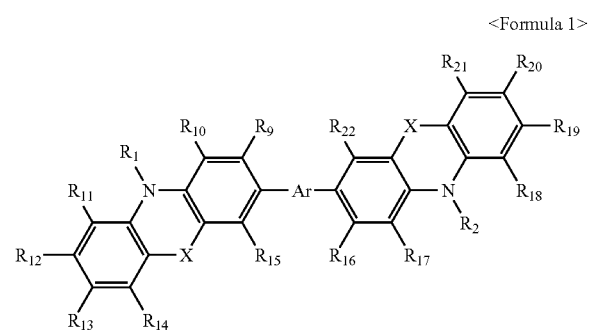

where Ar is a substituted or unsubstituted $C_6$-$C_{26}$ aryl group;

X is O, S,

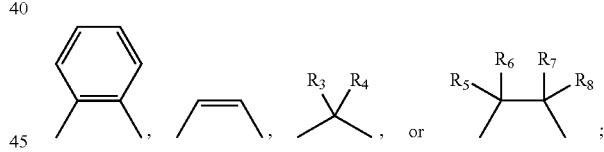

$R_1$ and $R_2$ are hydrogen, halogen, a substituted or unsubstituted $C_1$-$C_{12}$ alkyl group, or a substituted or unsubstituted $C_6$-$C_{26}$ aryl group;

$R_3$, $R_4$, $R_5$, $R_6$, $R_7$, and $R_8$ are each independently hydrogen or a substituted or unsubstituted $C_1$-$C_{12}$ alkyl group; and $R_9$ through $R_{22}$ are each independently selected from the group consisting of hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ arylalkyl group, a substituted or unsubstituted $C_6$-$C_{30}$ aryloxy group, a substituted or unsubstituted $C_5$-$C_{30}$ heteroaryl group, a substituted or unsubstituted $C_5$-$C_{30}$ heteroarylalkyl group, a substituted or unsubstituted $C_5$-$C_{30}$ heteroaryloxy group, a substituted or unsubstituted $C_5$-$C_{20}$ cycloalkyl group, and a substituted or unsubstituted $C_5$-$C_{30}$ heterocycloalkyl group.

The compound in Formula 1 may be included in an organic layer, for example, a light emitting layer, a hole injection layer, or a hole transport layer of an organic light emitting device.

Figure 2A:
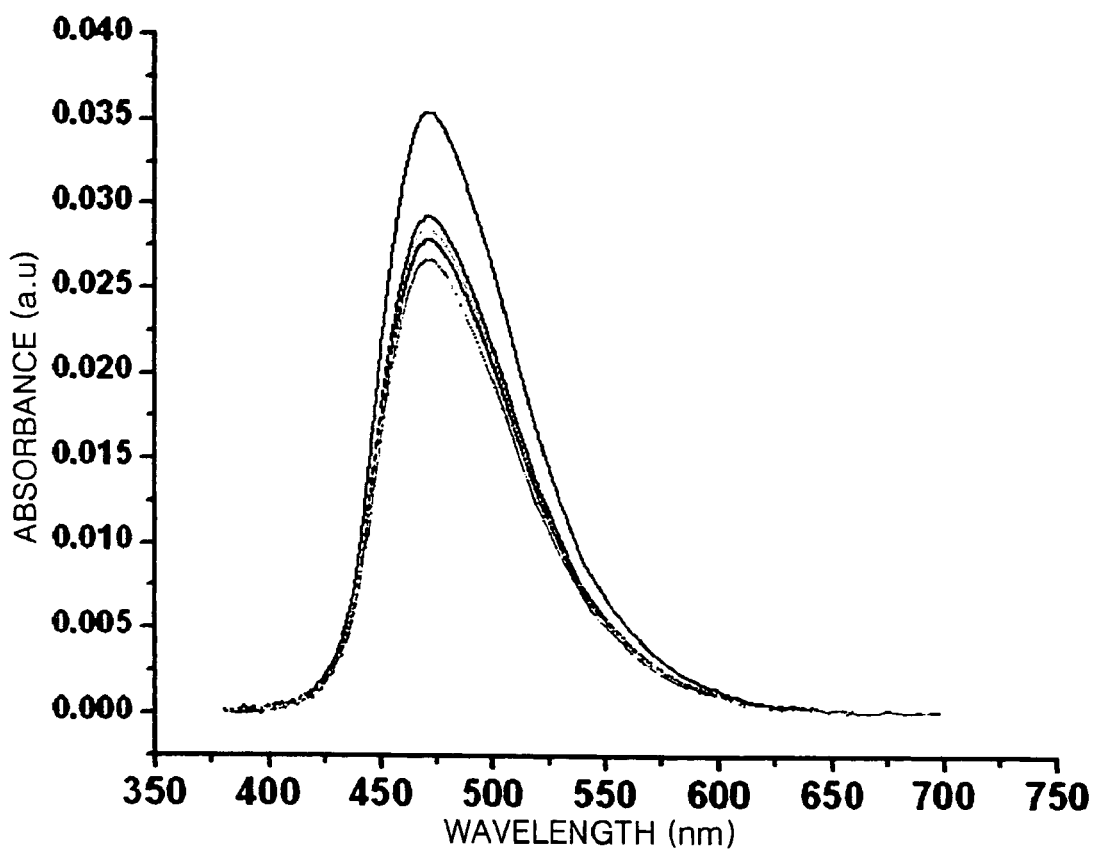
FIG. 2A is a graph showing photoluminescence (PL) spectra versus wavelength for a compound after a series of elapsed time periods according to an embodiment of the present invention and FIG. 2B is a normalized PL spectrum of FIG. 2A.
Figure 2B:
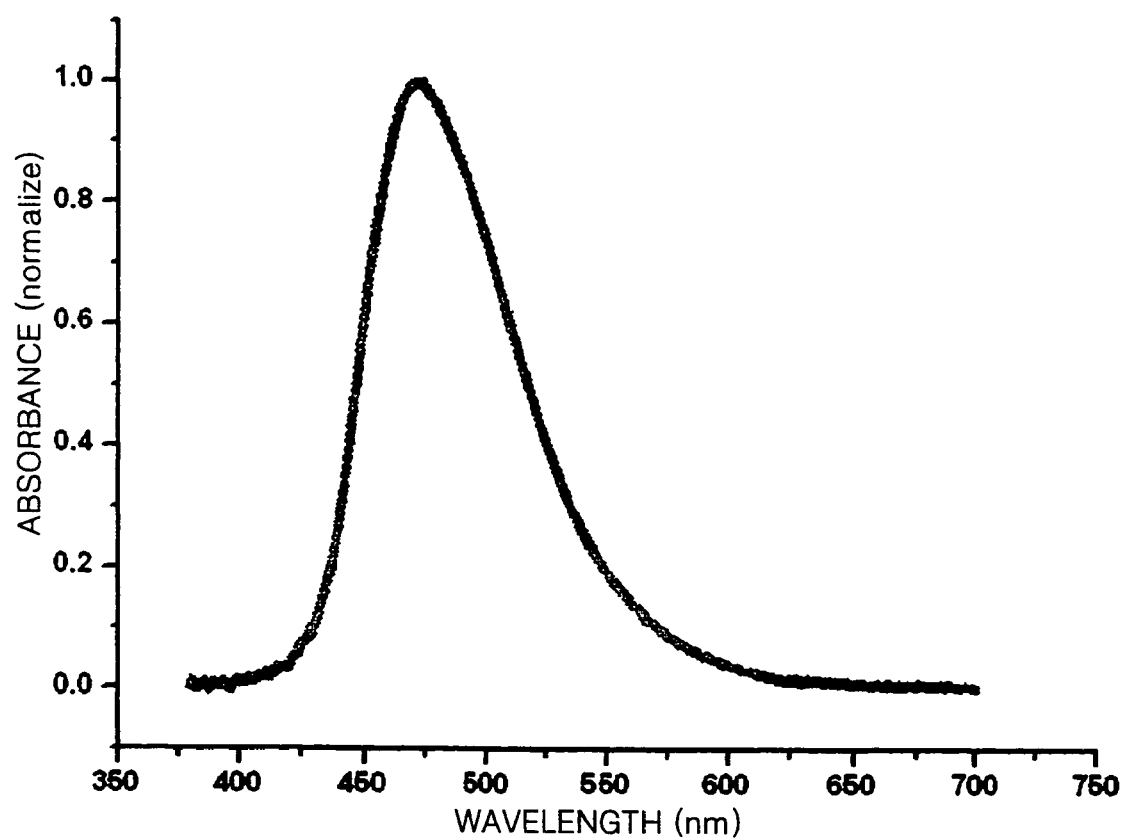

FIG. 2A is a graph showing photoluminescence (PL) spectra versus wavelength of compound 19 after a series of elapsed time periods according to an embodiment of the present invention and FIG. 2B is a graph showing normalized versions of the PL spectra of FIG. 2A.

In the case of a thin film manufactured using a spin coating method, changes of PL intensity of the compound after elapsed time periods are small and shapes of the spectra are the same as illustrated in FIG. 2B, thereby indicating excellent color stability of the thin film with respect to the time elapsed. Also, since photoluminescence quantum efficiency (PLQ) of the thin film is 33%, the thin film has good light emitting properties which are at least equal to conventional organic light emitting compounds.

When a conventional organic light emitting device is manufactured using a solution coating method, an organic layer included therein has low stability, however, the organic light emitting device according to the embodiments of the present invention includes an organic light emitting compound which was excellent solubility and thermal stability to form a stable organic layer, and provides improved light emitting properties such as low operating voltage and excellent color purity.

The organic light emitting device according to an embodiment of the present invention may have various structures. For example, the organic light emitting device may further include at least one layer interposed between the first electrode and the second electrode selected from the group consisting of a hole injection layer (HIL), a hole transport layer (HTL), an electron blocking layer (EBL), a hole blocking layer (HBL), an electron transport layer (ETL), and an electron injection layer (EIL).

Figure 1B:
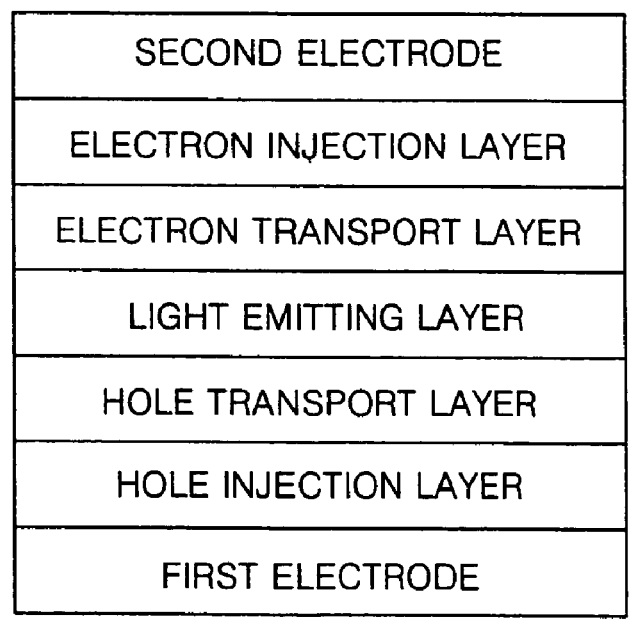
Figure 1C:
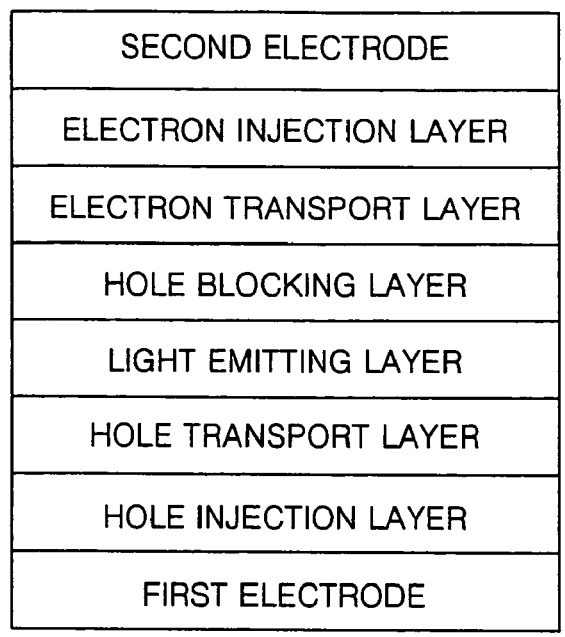

In particular, organic light emitting devices according to embodiments of the present invention are illustrated in FIGS. 1A, 1B, and 1C. FIG. 1A is a cross-sectional view of an organic light emitting device having a structure of first electrode/hole injection layer/light emitting layer (EML)/electron transport layer/electron injection layer/second electrode. FIG. 1B is a cross-sectional view of an organic light emitting device having a structure of first electrode/hole injection layer/hole transport layer/light emitting layer (EML)/electron transport layer/electron injection layer/second electrode. FIG. 1C is a sectional view of an organic light emitting device having the structure of first electrode/hole injection layer/hole transport layer/light emitting layer/hole blocking layer/electron transport layer/electron injection layer/second electrode. Here, at least one of a light emitting layer, a hole injection layer, and a hole transport layer may include a compound according to an embodiment of the present invention.

A light emitting layer of an organic light emitting device according to an embodiment of the present invention may contain a phosphorescent or fluorescent dopant which emits red, green, blue, or white light. Preferably, the phosphorescent dopant may include at least one organometallic compound selected from Ir, Pt, Os, Ti, Zr, Hf, Eu, Tb, and Tm.

Hereinafter, a method of manufacturing an organic light emitting device according to an embodiment of the present invention will now be described with reference to the organic light emitting device illustrated in FIG. 1C.

First, a material having high work function is deposited on the upper surface of a substrate using a deposition method or a sputtering method to form a first electrode. The first electrode may be an anode. Here, the substrate may be a substrate that is commonly used in a conventional organic light emitting device. For example, the substrate may be a glass substrate or a transparent plastic substrate which has excellent mechanical strength, thermal stability and surface smoothness, and are transparent, waterproof, and easily handled. The first electrode material may be a conductive transparent material such as indium tin oxide (ITO), indium zinc oxide (IZO), tin oxide ($SnO_2$), zinc oxide (ZnO), and the like.

Then, a hole injection layer (HIL) can be formed on the first electrode using various methods such as a vacuum deposition method, a spin coating method, a casting method, a Langmuir-Blodgett (LB) method, or the like.

When the HIL is formed using a vacuum deposition method, deposition conditions may vary according to HIL forming compounds and the structure and thermal properties of a HIL which is to be formed. For example, a deposition temperature may be in the range of 100 to 500° C., a pressure may be in the range of $10^{-8}$ to $10^{-3}$ torr, a deposition rate may be in the range of 0.01 to 100 Å/sec, and a thickness of the HIL may be in the range of 10 Å to 5 μm.

When the HIL is formed using a spin coating method, coating conditions may vary according to HIL forming compounds and the structure and thermal properties of a HIL which is to be formed. For example, a coating speed may be in the range of about 2000 rpm to 5000 rpm and a heat treatment temperature for removing a solvent after the coating may be in the range of about 80° C. to 200° C.

Material used to form the HIL may be a compound represented by Formula 1, or a phthalocyanine compound such as copper phthalocyanine disclosed in U.S. Pat. No. 4,356,429, a starburst type amine derivative such as TCTA, m-MTDATA, and m-MTDAPB disclosed in Advanced Material, 6, p. 677 (1994), a conductive soluble polymer such as polyaniline/dodecylbenzenesulfonic acid (Pani/DBSA), or disclosed hole injection materials such as poly(3,4-ethylenedioxythiophene)/poly(4-styrenesulfonate) (PEDOT/PSS), polyaniline/camphor sulfonic acid (Pani/CSA) or (polyaniline)/poly(4-styrenesulfonate (PANI/PSS).

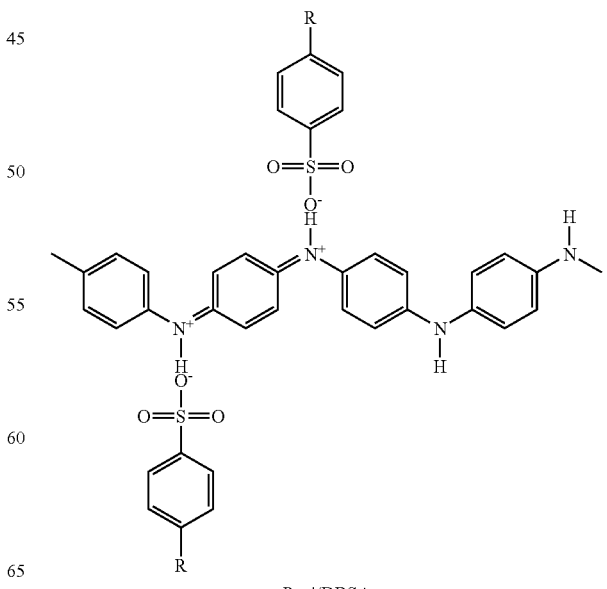

Pani/DBSA

-continued

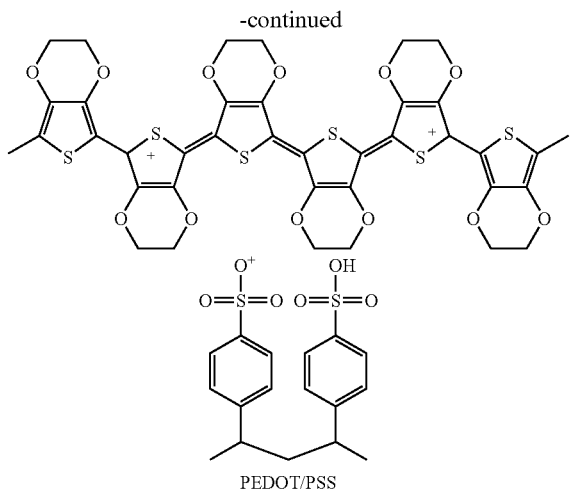

PEDOT/PSS

The thickness of the HIL may be in the range of about 100 to 10,000 Å, for example, 100 to 1,000 Å. When the thickness of the HIL is below 100 Å, a hole injecting property may be degraded. When the thickness of the HIL is above 10,000 Å, the operating voltage may be increased.

Subsequently, a hole transport layer (HTL) can be formed on the HIL using various methods such as vacuum deposition, spin coating, casting, LB, or the like. When the HTL is formed using a vacuum deposition method or a spin coating method, vacuum deposition conditions or spin coating conditions may vary according to HTL forming compounds and may be almost the same as when the HIL is formed.

The HTL may be formed of a compound represented by Formula 1 as described above. For example, the HTL may be formed of a carbazole derivative such as N-phenylcarbazole, polyvinylcarbazole, or the like, a conventional amine derivative having an aromatic condensation ring such as N,N'-bis (3-methylphenyl)-N,N'-diphenyl-[1,1-biphenyl]-4,4'-diamine(TPD), N,N'-di(naphthalene-1-yl)-N,N'-diphenyl benzidine (α-NPD), or the like.

The thickness of the HTL may be in the range of about 50 to 1000 Å, for example, 100 to 600 Å. When the thickness of the HTL is less than 50 Å, a hole transport property may be degraded. When the thickness of the HTL is above 1000 Å, the operating voltage may be increased.

Then, a light emitting layer (EML) can be formed on the HTL using various methods such as vacuum deposition, spin coating, casting, LB, or the like. When the EML is formed using a vacuum deposition method or spin coating method, vacuum deposition conditions or spin coating conditions may vary according to EML forming compounds and may be almost the same as when the HIL is formed.

The EML may include a compound in Formula 1 as described above. The compound in formula 1 can be used together with a host material or a dopant material. The compound in Formula 1 can be used by itself. Examples of the host material may be tris(8-quinolinolate)aluminum ($Alq_3$), CBP(4,4'-N,N'-dicarbazole-biphenyl), or PVK(poly(n-vinylcarbazole)), but are not limited thereto. Examples of the dopant material may be IDE102, IDE105 (produced by Idemitsu Inc) and C545T (produced by Hayashibara Inc.) as a fluorescent dopant and PtOEP, RD 61 (produced by UDC Inc.) which are red phosphorescent dopants, $Ir(PPy)_3$(PPy=2-phenylpyridine) which are green phosphorescent dopants, and F2Irpic, RD 61 (produced by UDC Inc.) which are blue phosphorescent dopants as a phosphorescent dopant, but are not limited thereto. The structure of DPAVBi which can be used as a dopant is illustrated in Formula 22.

[Formula 22]

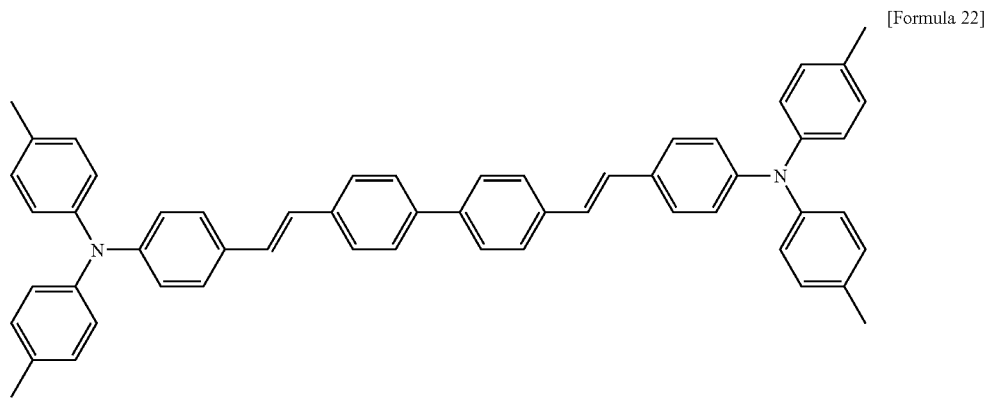

The concentration of the dopant is not particularly restricted but may be 0.01 to 15 parts by weight based on 100 parts by weight of a host.

The thickness of the EML may be in the range of 100 to 1.000 Å, for example, 200 to 600 Å. When the thickness of the EML is below 100 Å, a light emitting property may be degraded. When the thickness of the EML is above 1,000 Å, the operating voltage may be increased.

When the EML is formed using a phosphorescent dopant, a hole blocking layer (HBL) can be formed on the HTL using a vacuum deposition method, a spin coating method, a casting method, a LB method, or the like to prevent diffusion of triplet excimers or holes into an electron transport layer. When the HBL is formed using a vacuum deposition or a spin coating, the vacuum deposition conditions or spin coating conditions may vary according to compounds used to form the HBL and may be almost the same as when the HIL is formed. Also, the HBL may be formed of a compound represented by Formula 1. A known hole blocking material may be, for example, an oxadiazole derivative, a triazole derivative, a phenanthroline derivative, BCP, or the like.

The thickness of the HBL may be in the range of about 50 to 1,000 Å, for example, 100 to 300 Å. When the thickness of the HBL is below 50 Å, a hole blocking property may be degraded. When the thickness of the HBL is above 1,000 Å, the operating voltage may be increased.

Subsequently, an electron transport layer (ETL) can be formed using various methods such as a vacuum deposition method, a spin coating method, a casting method, or the like. When the ETL is formed using vacuum deposition or spin coating, the vacuum deposition conditions or spin coating conditions may vary according to compounds used to form the ETL and may be almost the same as when the HIL is formed. The compound used to form the ETL stably transports electrons injected from an electron injection electrode (cathode) and may be a quinoline derivative, for example, tris(8-quinolinolate)aluminum($Alq_3$) or 3-(4-biphenyl)-4-phenyl-5-(4-tert-butylphenyl)-1,2,4-triazole (TAZ).

The thickness of the ETL may be in the range of about 100 to 1,000 Å, for example, 200 to 500 Å. When the thickness of the ETL is below 100 Å, an electron transporting property may be degraded. When the thickness of the ETL is above 1,000 Å, the operating voltage may increase.

An electron injection layer (EIL), which allows easy injection of electrons from a cathode, can be formed on the ETL. A material used to form the EIL is not limited.

The EIL can be formed of any known materials used conventionally to form an EIL such as LiF, NaCl, CsF, $Li_2O$, BaO, or the like. The vacuum deposition conditions for the EIL may vary according to compounds used to form the EIL and may be almost the same as when the HIL is formed.

The thickness of the EIL may be in the range of about 1 to 100 Å, for example, 5 to 50 Å. When the thickness of the EIL is below 1 Å, an electron injecting property may decrease. When the thickness of the EIL is above 100 Å, the operating voltage may increase.

Last, a second electrode can be formed on the EIL using a vacuum deposition method or a sputtering method. The second electrode can be used as a cathode. A second electrode may be formed of a metal, an alloy, an electrically conductive compound, or a mixture thereof which has a low work function. Examples of the second electrode forming metal are Li, Mg, Al, Al—Li, Ca, Mg—In, Mg—Ag, or the like. In addition, in order to obtain a front emission type light emitting device, a light transmissive cathode formed of ITO and IZO can be used.

The present invention will be described in greater detail with reference to the following examples. The following examples are for illustrative purposes and are not intended to limit the scope of the invention.

SYNTHESIS EXAMPLE 1

According to a reaction path of Reaction Scheme 1, compound 19 represented by Formula 19 was synthesized:

[Reaction Scheme 1]

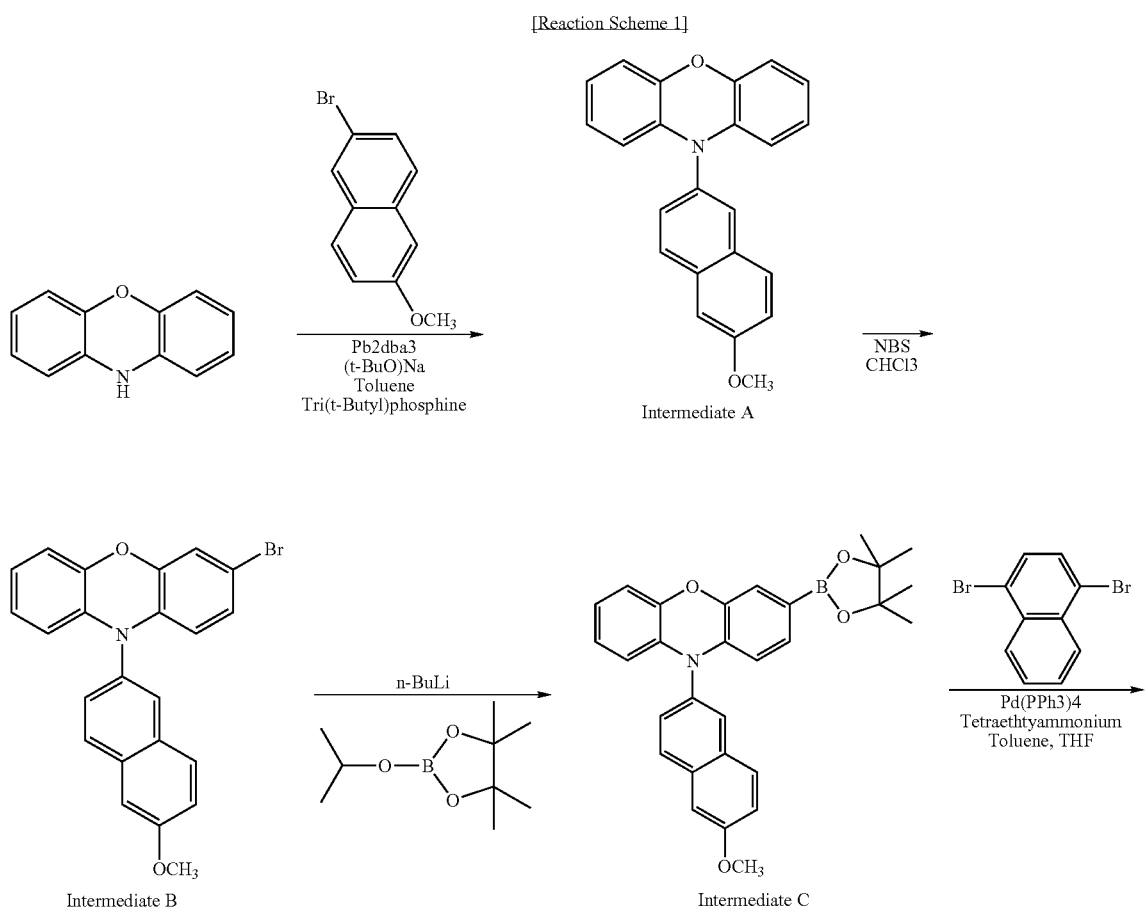

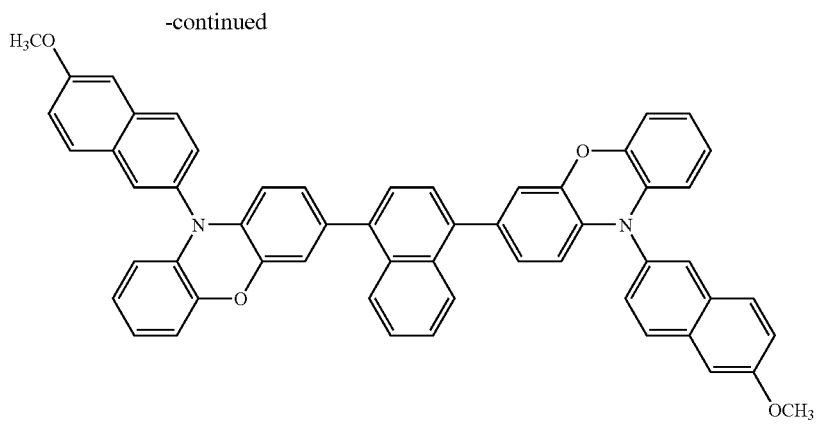

Compound 19

Synthesis of Compound 19

Synthesis of Intermediate A 7.5 g (32 mmol) of 2-bromo-6-methoxynaphthalene, 4.6 g (25 mmol) of phenoxazine, 3.7 g (38 mmol) of sodium tert-butoxide ((t-BuO)Na), 0.3 g (0.33 mmol) of $Pd_2(dba)_3$ [(tris(dibenzylidine acetone) dipalladium (0))], and 0.11 g (0.55 mmol) of tri(tert-butyl)phosphine were dissolved in 125 mL of toluene and were reacted for 12 hours at 80° C.

After the reaction was completed, the reaction mixture was cooled down to an ambient temperature and 200 ml of distilled water was added and quenched. Then, xylene and water were extracted in the volume ratio of 1:1.

The collected organic layer was dried and concentrated using $MgSO_4$ and a column chromatography was performed using an eluant formed of toluene and hexane in the volume ratio of 1:2. The obtained effluent was concentrated and dried to obtain 6.8 g (Yield: 80%) of intermediate A. The structure of intermediate A was identified through 1H NMR spectroscopy.

Synthesis of Intermediate B 3.39 g (10 mmol) of intermediate A was dissolved in 150 ml of $CHCl_3$ and bromine 1.1 equivalent was slowly added to intermediate A while maintaining the temperature of 0° C. When the starting material had completely dissolved according to thin layer chromatography (TLC) confirmation, the addition of bromine into the mixture above was stopped and the reaction mixture was stirred for 10 minutes, then the reaction was stopped.

A small amount of acetone was added to the above reaction mixture to quench the brome and extraction was performed thereto using water and $CHCl_3$ with the volume ration of 2:1. The collected organic layer was dried and concentrated using $MgSO_4$ and re-precipitated in MeOH to obtain 4.2 g (Yield: 85%) of intermediate B. The structure of intermediate B was identified through 1H NMR spectroscopy.

Synthesis of Intermediate C 1.095 g (1.0 eq, 2.72 mmol) of intermediate B was put in a 50 ml of round bottom flask to dissolve in 10 ml of tetrahydrofuran (THF) and the resultant was cooled down to –78° C. 2.2 ml (2.0 eq, 5.44 mmol) of n-BuLi 2.5M (hexane) was slowly dropped in the resultant solution and stirred for 30 minutes while maintaining the temperature of –78° C. Then, 1.1 ml (2.0 eq, 5.44 mmol) of 2-isopropoxy-4,4,5,5-tetramethyl-1,3,2-dioxabororane was added and the reaction temperature was gradually raised (1 hour and 30 minutes) to room temperature while stirring. The resultant was stirred for 30 minutes once again at room temperature and then, 10 ml of water and 10 ml of ethylacetate were extracted. An aqueous solution liquid layer was extracted using 10 ml of $CHCl_3$ and an organic layer was added thereto to dry and concentrate using $MgSO_4$. Then, 0.76 g (60%) of intermediate C was separated from the resultant product above using a silica column chromatography in which the mixed solution of ethylacetate and hexane with the mixed ratio of 3:22 was used as a developing solution. The structure of intermediate C was identified through 1H NMR spectroscopy.

Synthesis of Compound 19

100 mg (0.215 mmol) of intermediate C was dissolved in 1 ml of THF and then, a mixture of 24.6 mg (0.086 mmol) of 1,4-dibromobenzene and 10 mg (0.009 mmol) of tetrakis(triphenylphosphine)palladium(0) $(Pd(PPh_3)_4)$ dissolved in 2 ml of toluene was added thereto. 2 ml of 20% tetraethyl ammonium aqueous solution was added to the mixed solution and the mixed solution was stirred for 24 hours at 100° C. After cooling down the resultant to room temperature, the resultant product was separated and purified using a absorption silica gel column chromatography to obtain 69.0 mg of compound 19 (Yield: 95%). The structure of Compound 19 was identified through 1H NMR spectroscopy.

$^1$H-NMR (300 MHz, $CDCl_3$): δ7.67 (d, 2H), δ7.60 (dd, 2H), δ7.44 (d, 2H), δ7.37 (s, 2H), δ7.32 (s, 2H), δ6.95 (m, 4H), δ6.89 (m, 2H), δ6.85 (m, 2H), δ6.76 (m, 4H), δ6.73 (m, 2H), δ6.67 (m, 2H), δ6.58 (m, 2H), δ6.48 (m, 2H), δ6.42 (m, 2H), δ3.73 (m, 6H)

SYNTHESIS EXAMPLE 2

A compound 5 represented by Formula 5 was synthesized:

A compound 5 represented by Formula 5 was synthesized in the same manner as compound 19 in Synthesis of Compound 19, except that bromobenzene and 1,4-dibromobenzene were used instead of 2-bromo-6-methoxynaphthalene and 1,4-dibromonaphthalene, respectively. Consequently, 75 mg (Yield: 89%) of compound 5 was obtained.

$^1$H-NMR (300 MHz, $CDCl_3$): δ7.54 (d, 4H), δ7.01 (dd, 4H), δ6.95 (d, 2H), δ6.89 (s, 2H), δ6.73 (s, 2H), δ6.67 (m, 2H), δ6.62 (m, 2H), δ6.58 (m, 2H), δ6.48 (m, 2H), δ6.46 (m, 4H), δ6.42 (m, 2H)

SYNTHESIS EXAMPLE 3

A compound 17 represented by Formula 17 was synthesized:

A compound 17 represented by Formula 17 was synthesized in the same manner as compound 19 in Synthesis of Compound 19, except that diiminobenzyl, 2-bromonaphthalene, and 9,10-dibromoanthracene were used instead of phenoxazine, 2-bromo-6-methoxynaphthalene, and 1,4-dibromonaphthalene, respectively. Consequently, 120 mg (Yield: 75%) of compound 17 was obtained.

$^1$H-NMR (300 MHz, CDCl$_3$): δ7.91 (d, 4H), δ7.55 (d, 2H), δ7.51 (d, 2H), δ7.44 (s, 2H), δ7.39 (m, 4H), δ7.23 (m, 2H), δ7.09 (m, 4H), δ7.05 (m, 5H), δ6.83 (m, 2H), δ6.79 (m, 2H), δ6.76 (m, 4H), δ6.57 (m, 2H), δ6.47 (m, 2H), δ6.41 (m, 2H), δ2.88 (d, 4H)

EVALUATION EXAMPLE 1

Light Emitting Property of Compound

UV absorption spectra and photoluminescence (PL) spectra of compounds were measured to determine light emitting properties of respective compounds. First, compound 5 was diluted using toluene to have a concentration of 0.2 mM, and a UV absorption spectrum of compound 5 was measured using a Shimadzu UV-350 spectrometer. A UV absorption spectrum was measured for each of compounds 7, 9, 11, 17, 18, 19, 20 and 21. Then, compound 5 was diluted using toluene to have a concentration of 10 mM, and a PL spectrum of compound 5 was measured using an ISC PC1 spectrofluorometer equipped with a Xenon lamp. The results are shown in Table 1.

In addition, FIG. 2A shows photoluminescence (PL) spectra versus wavelength of the compound after a series of elapsed time periods and FIG. 2B is a graph showing normalized versions of the PL spectra of FIG. 2A.

In the case of a thin film manufactured using a spin coating method, changes of PL intensity of the compound after elapsed time periods are small and shapes of the spectra are the same as illustrated in FIG. 2B, thereby indicating excellent color stability of the thin film with respect to the time elapsed. Also, since a PLQ of the thin film is 33%, the thin film has good light emitting properties which are nearly identical with conventional organic light emitting compounds.

TABLE 1

| Compound No. | UV absorption(nm) | PL(nm) |
| --- | --- | --- |
| 5 | 370 | 438 |
| 7 | 332, 360 | 444 |
| 9 | 370, 390 | 476 |
| 11 | 382 | 472 |
| 17 | 379 | 465 |
| 18 | 376 | 443 |
| 19 | 332, 364 | 450 |
| 20 | 376, 398 | 482 |
| 21 | 385 | 470 |

EXAMPLE 1

An organic light-emitting device was manufactured using compound 19 represented by Formula 19 as a dopant of a light emitting layer and compound 23 represented by Formula 23 (AND) as a host of a light emitting layer. The structure of the organic light emitting device is ITO/PEDOT(500 Å)/AND+compound 19(480 Å)/Alq3(200 Å)/LiF(10 Å)/Al(2000 Å).

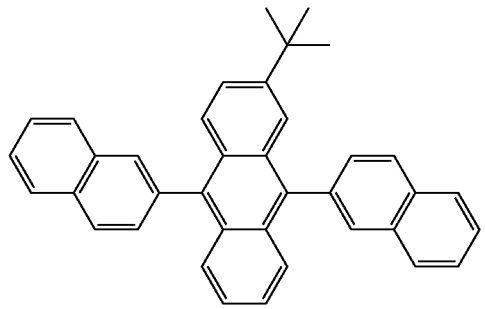

[Formula 23]

In order to prepare an anode, an ITO glass substrate 15 Ω/cm$^2$ (1200 Å) was cut to a size of 50 mm×50 mm×0.7 mm, sonicated using isopropyl alcohol and pure water for 15 minutes each respectively, and washed using ultra violet (UV) ozone for 30 minutes. Then, PEDOT-PSS (AI4083) produced by Bayer Inc. was coated on the prepared anode, heat treated at 110° C. for 5 minutes, and heat treated again in a nitrogen atmosphere at 200° C. for 5 minutes to form a HIL having a thickness of 500 Å. A mixture of 0.1 g of host compound 5 (AND) and 0.05 g of dopant compound 19 (5 parts by weight of compound 19 represented by Formula 19 based on 100 parts by weight of the compound (AND)) was spin coated on the HIL and then heat treated at 100° C. for 30 minutes to form an EML having a thickness of 480 Å. Then, an Alq3 compound was vacuum deposited on the EML to form an ETL. LiF was vacuum deposited on the ETL to form an EIL having a thickness of 10 Å and then Al was vacuum deposited on the EIL to form a cathode having a thickness of 2000 Å. As a result, manufacture of an organic light emitting device illustrated in FIG. 1A was completed. The obtained organic light emitting device will be referred to as Sample 1.

EXAMPLE 2

An organic light emitting device having the structure of ITO/PEDOT (500 Å)/compound 19(480 Å)/Alq3(200 Å)/LiF(10 Å)/Al(2000 Å) was manufactured in the same manner as in Example 1, except that AND as a host was not used, only compound 19 was used as an light emitting layer. The obtained organic light emitting device will be referred to as Sample 2.

EXAMPLE 3

An organic light emitting device having the structure of ITO/PEDOT(500 Å)/AND+compound 17(480 Å)/Alq3(200 Å)/LiF(10 Å)/Al(2000 Å) was manufactured in the same manner as in Example 1, except that compound 17 was used instead of compound 19 as a dopant. The obtained organic light emitting device will be referred to as Sample 3.

COMPARATIVE EXAMPLE 1

An organic light emitting device having the structure of ITO/PEDOT(500 Å)/AND+compound 22(480 Å)/Alq3(200 Å)/LiF(10 Å)/Al(2000 Å) was manufactured in the same manner as in Example 1, except that AND as a host and compound 22 (DPAVBi) of Formula 22 as a dopant were used. The obtained organic light emitting device will be referred to as Sample 4.

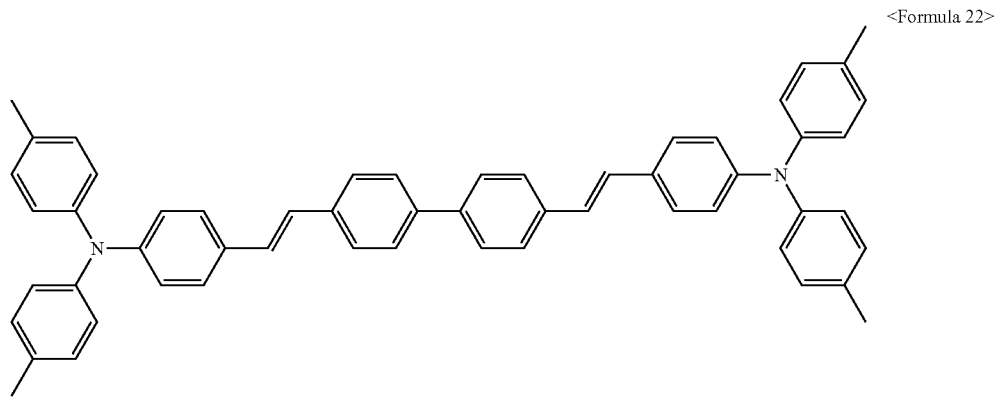

<Formula 22>

EVALUATION EXAMPLE 2

Properties of Samples 1, 2, 3 and 4

Operating voltages, color purities, and efficiencies of Samples 1 through 3 and comparative sample 4 were measured using a PR650 (Spectroscan) Source Measurement Unit. The results are shown in Table 2.

TABLE 2

| Sample No. | Turn on voltage(V) | CIE color coordinate(~100 cd/m$^2$) | Efficiency (cd/A) |
|---|---|---|---|
| 1 | 3.2 | (0.15, 0.24) | 5.4 V to 6.02 |
| 2 | 3.6 | (0.15, 0.22) | 5.0 V to 4.60 |
| 3 | 3.4 | (0.16, 0.12) | 5.8 V to 2.61 |
| 4 | 3.4 | (0.15, 0.27) | 5.4 V to 4.16 |

As illustrated in Table 2, samples 1 through 3 according to the embodiments of the present invention have excellent light emitting properties.

A compound represented by formula 1 according to the embodiment of the present invention has excellent solubility, light emitting properties, and thermal stability. Accordingly, an organic light emitting device using the compound has a low operating voltage and high color purity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organic light emitting compound represented by Formula 1:

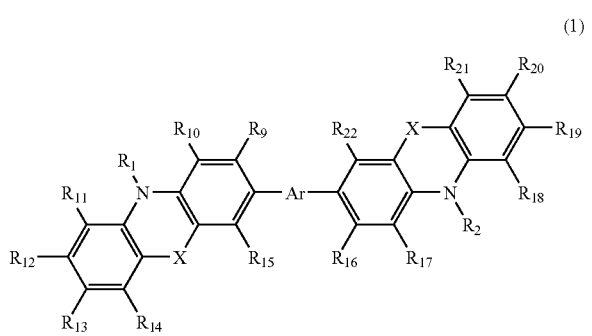

(1)

where Ar is naphthalene;

X is O, and S;

$R_1$ and $R_2$ are hydrogen, a halogen, a substituted or unsubstituted $C_1$-$C_{12}$ alkyl group, or a substituted or unsubstituted $C_6$-$C_{26}$ aryl group;

$R_3$, $R_4$, $R_5$, $R_6$, $R_7$ and $R_8$ are each independently hydrogen or a substituted or unsubstituted $C_1$-$C_{12}$ alkyl group; and $R_9$ through $R_{22}$ are each independently selected from the group consisting of hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ arylalkyl group, a substituted or unsubstituted $C_6$-$C_{30}$ aryloxy group, a substituted or unsubstituted $C_5$-$C_{30}$ heteroaryl group, a substituted or unsubstituted $C_5$-$C_{30}$ heteroarylalkyl group, a substituted or unsubstituted $C_5$-$C_{30}$ heteroaryloxy group, a substituted or unsubstituted $C_5$-$C_{20}$ cycloalkyl group, and a substituted or unsubstituted $C_5$-$C_{30}$ heterocycloalkyl group.

2. The organic light emitting compound of claim 1, wherein the compound is represented by Formula 2:

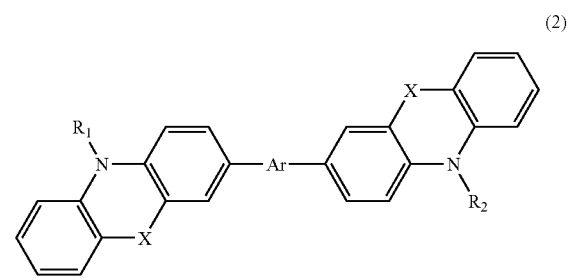

(2)

where Ar is naphthalene;

X is O, and S;

$R_1$ and $R_2$ are hydrogen, a halogen, a substituted or unsubstituted $C_1$-$C_{12}$ alkyl group, or a substituted or unsubstituted $C_6$-$C_{26}$ aryl group; and $R_3$, $R_4$, $R_5$, $R_6$, $R_7$ and $R_8$ are each independently hydrogen or a substituted or unsubstituted $C_6$-$C_{12}$ alkyl group.

3. The organic light emitting compound of claim 1, wherein the compound is represented by Formula 3:

(3)

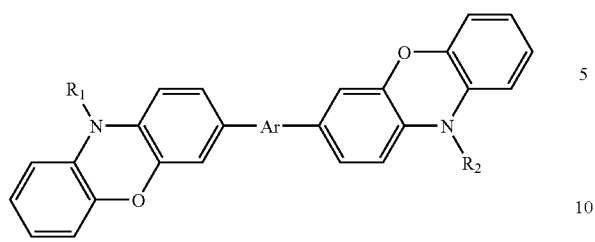

where Ar is naphthalene; and
R$_1$ and R$_2$ are hydrogen, a halogen, a substituted or unsubstituted C$_1$-C$_{12}$ alkyl group, or a substituted or unsubstituted C$_6$-C$_{26}$ aryl group.

4. The organic light emitting compound of claim 1, wherein Ar is

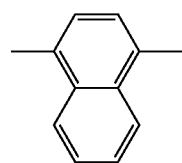

5. The organic light emitting compound of claim 1, wherein the compound is represented by one selected from the group consisting of Formulas 7, 8 and 19:

(7)

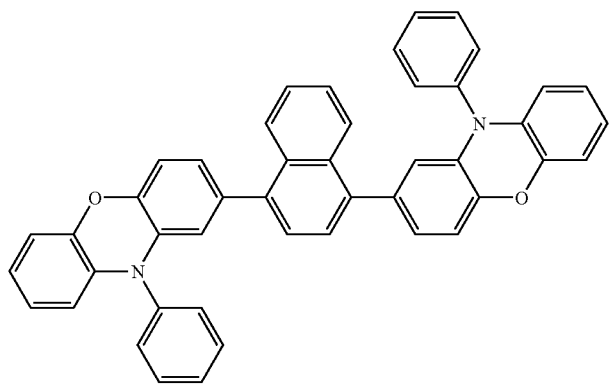

(8)

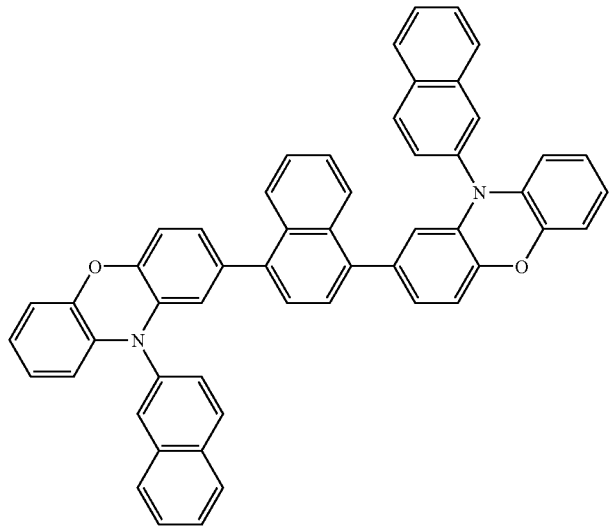

(19)

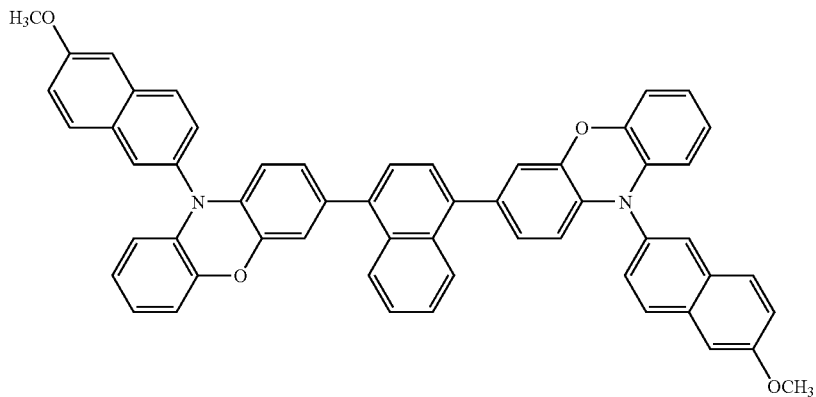

6. An organic light emitting device including an organic layer having the organic light emitting compound of claim 1.

7. An organic light emitting device, comprising:
a first electrode;
a second electrode; and
at least one organic layer interposed between the first electrode and the second electrode, said at least one organic layer comprising an organic light emitting compound represented by Formula 1:

(1)

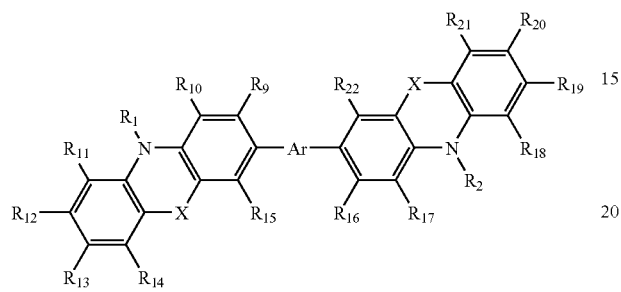

where Ar is naphthalene;
X is O, and S;
$R_1$ and $R_2$ are hydrogen, a halogen, a substituted or unsubstituted $C_1$-$C_{12}$ alkyl group, or a substituted or unsubstituted $C_6$-$C_{26}$ aryl group;
$R_3$, $R_4$, $R_5$, $R_6$, $R_7$ and $R_8$ are each independently hydrogen or a substituted or unsubstituted $C_1$-$C_{12}$ alkyl group; and
$R_9$ through $R_{22}$ are each independently selected from the group consisting of hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ arylalkyl group, a substituted or unsubstituted $C_6$-$C_{30}$ aryloxy group, a substituted or unsubstituted $C5$-$C_{30}$ heteroaryl group, a substituted or unsubstituted $C5$-$C_{30}$ heteroarylalkyl group, a substituted or unsubstituted $C5$-$C_{30}$ heteroaryloxy group, a substituted or unsubstituted $C_5$-$C_{20}$ cycloalkyl group, and a substituted or unsubstituted $C_5$-$C_{30}$ heterocycloalkyl group.

8. The organic light emitting device of claim 7, wherein said at least one organic layer comprises at least one of a light emitting layer, a hole injection layer, and a hole transport layer.

9. The organic light emitting device of claim 7, wherein said at least one organic layer is a light emitting layer formed of the organic light emitting compound.

10. The organic light emitting device of claim 7, wherein said at least one organic layer comprises a light emitting layer and a hole injection layer formed of the organic light emitting compound.

11. The organic light emitting device of claim 7, wherein at least one organic layer comprises a light emitting layer and a hole transport layer formed of the organic light emitting compound.

12. The organic light emitting device of claim 7, wherein the organic light emitting compound is represented by one selected from the group consisting of Formula 2, and Formula 3:

(2)

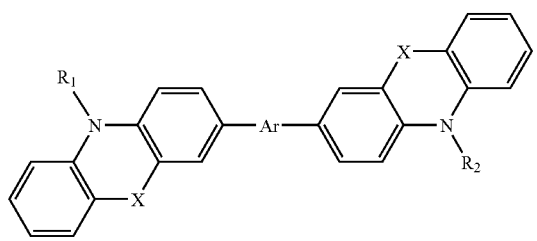

where Ar is naphthalene;
X is O, and S;
$R_1$ and $R_2$ are hydrogen, a halogen, a substituted or unsubstituted $C_1$-$C_{12}$ alkyl group, or a substituted or unsubstituted $C_6$-$C_{26}$ aryl group; and
$R_3$, $R_4$, $R_5$, $R_6$, $R_7$ and $R_8$ are each independently hydrogen or a substituted or unsubstituted $C_6$-$C_{12}$ alkyl group;

(3)

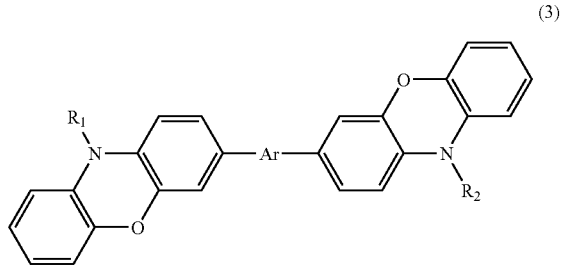

where Ar is naphthalene; and
$R_1$ and $R_2$ are hydrogen, a halogen, a substituted or unsubstituted $C_1$-$C_{12}$ alkyl group, or a substituted or unsubstituted $C_6$-$C_{26}$ aryl group.

13. The organic light emitting device of claim 7, wherein the organic light emitting compound is represented by one selected from the group consisting of Formulas 7, 8 and 19:

(7)

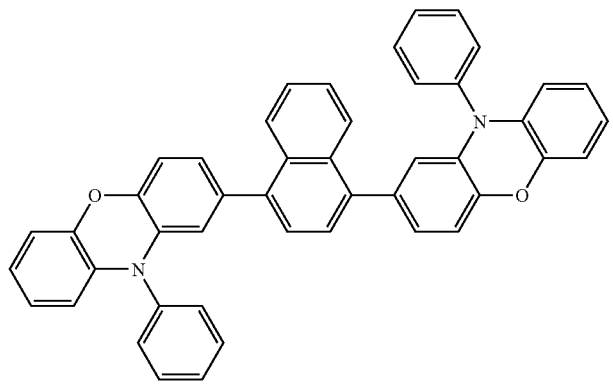

(8)

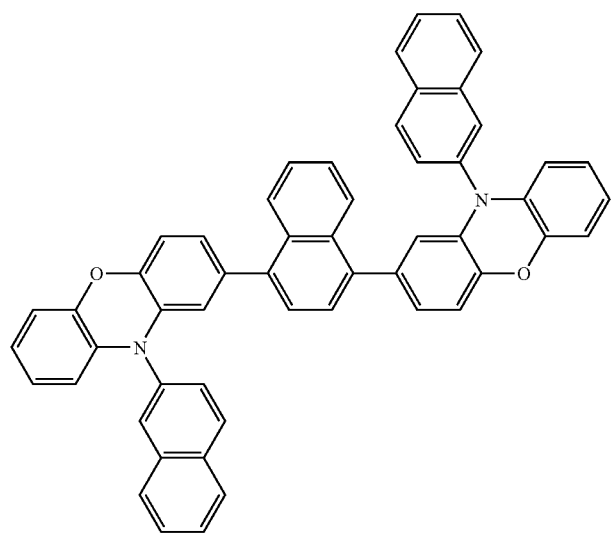

(19)

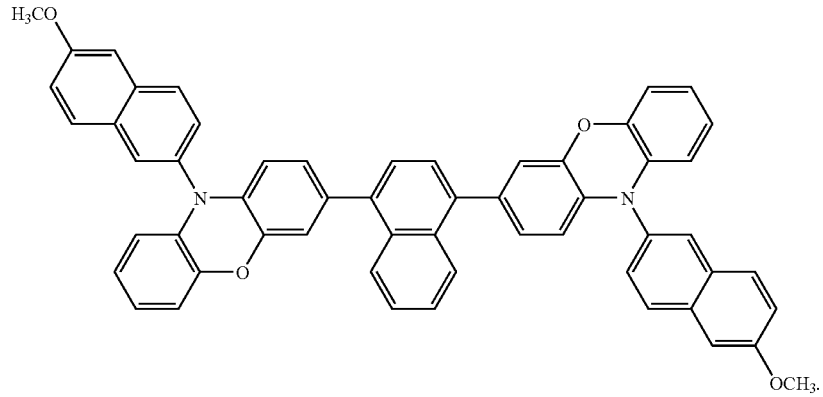

14. The organic light emitting device of claim 7, further comprising at least one layer which is interposed between the first electrode and the second electrode and which is selected from the group consisting of an electron blocking layer, a hole blocking layer, an electron transport layer, and an electron injection layer.

15. The organic light emitting device of claim 14, wherein the device has at least one structure selected from the group consisting of a structure of the first electrode/a hole injection layer/a light emitting layer/the electron transport layer/the electron injection layer/the second electrode, a structure of the first electrode/the hole injection layer/a hole transport layer/the light emitting layer/the electron transport layer/the electron injection layer/the second electrode, and a structure of the first electrode/the hole injection layer/the hole transport layer/the light emitting layer/the hole blocking layer/the electron transport layer/the electron injection layer/the second electrode.

16. The organic light emitting device of claim 7, further comprising at least one of a hole transport layer and a hole injection layer which are interposed between the first electrode and the light emitting layer and which are formed of the organic light emitting compound.

17. The organic light emitting device of claim 7, wherein the light emitting layer comprises a host doped with a dopant of the organic light emitting compound.

* * * * *